United States Patent
Durocher

(10) Patent No.: US 9,370,222 B2
(45) Date of Patent: Jun. 21, 2016

(54) PREFORM AND DEVICE FOR COOPERATION WITH A LOWER LIMB MEMBER, APPARATUS AND METHOD FOR MANUFACTURING THE DEVICE

(75) Inventor: Philippe Durocher, Quebec (CA)

(73) Assignee: ORTHO-DURO INC., Montreal, Quebec (CA)

( * ) Notice: Subject to any disclaimer, the term of this patent is extended or adjusted under 35 U.S.C. 154(b) by 472 days.

(21) Appl. No.: 13/996,091

(22) PCT Filed: Dec. 20, 2011

(86) PCT No.: PCT/CA2011/001424
§ 371 (c)(1),
(2), (4) Date: Jun. 20, 2013

(87) PCT Pub. No.: WO2012/083443
PCT Pub. Date: Jun. 28, 2012

(65) Prior Publication Data
US 2013/0263470 A1 Oct. 10, 2013

Related U.S. Application Data

(60) Provisional application No. 61/426,641, filed on Dec. 23, 2010.

(51) Int. Cl.
*A43B 13/38* (2006.01)
*A43B 7/14* (2006.01)
(Continued)

(52) U.S. Cl.
CPC ............... *A43B 13/38* (2013.01); *A43B 7/142* (2013.01); *A43B 7/143* (2013.01); *A43B 7/1445* (2013.01); *A43B 7/1465* (2013.01); *A43B 7/223* (2013.01); *A43B 17/14* (2013.01); *A43D 1/022* (2013.01); *A43D 39/00* (2013.01); *A61F 5/14* (2013.01); *B29D 35/122* (2013.01)

(58) Field of Classification Search
CPC .......... A43B 7/28; A43B 7/142; A43B 7/143; A43B 7/1445; A43B 7/1465; A43B 7/223; A61F 5/14; B29D 35/122
USPC ............................................. 36/153, 154, 29
See application file for complete search history.

(56) References Cited

U.S. PATENT DOCUMENTS 2,546,827 A * 3/1951 Lavinthal ............... A43B 7/142
36/154
3,121,430 A 2/1964 O'Reilly
(Continued)

FOREIGN PATENT DOCUMENTS

EP 0310531 A1 4/1989
FR 2659535 A1 9/1991

*Primary Examiner* — Ted Kavanaugh
(74) *Attorney, Agent, or Firm* — Ware, Fressola, Maguire & Barber LLP

(57) ABSTRACT

The invention concerns a preform and a device for cooperating with a lower limb member so as to provide a correction to the limb member. The invention also concerns a method and an apparatus for manufacturing the device. The preform comprises a base, a surface linked to the top face of the base, for cooperation with the lower limb; and at least one inflatable chamber formed by a flexible and liquid-impervious membrane sealed to the concave top face of the base. Injection of a fluid composition of curable material, while the lower limb member is in contact with the surface so as to inflate the at least one inflatable chamber is performed until the correction is obtained, the composition being then cured in-situ into a cured material.

28 Claims, 8 Drawing Sheets

(51) Int. Cl.
  *A43B 7/22* (2006.01)
  *A43B 17/14* (2006.01)
  *A43D 1/02* (2006.01)
  *A61F 5/14* (2006.01)
  *B29D 35/12* (2010.01)
  *A43D 39/00* (2006.01)

(56) References Cited

U.S. PATENT DOCUMENTS

| | | | |
|---|---|---|---|
| 3,444,586 A | 5/1969 | Dubner | |
| 3,561,141 A * | 2/1971 | Brown | A43B 7/141 36/44 |
| 3,985,853 A * | 10/1976 | Weisberg | A61F 5/14 264/223 |
| 4,128,951 A | 12/1978 | Tansill | |
| 4,211,019 A | 7/1980 | McCafferty | |
| 4,385,024 A * | 5/1983 | Tansill | A43B 7/28 264/223 |
| 4,470,782 A | 9/1984 | Zimmerman, Jr. et al. | |
| 4,962,762 A | 10/1990 | Beekil | |
| 5,042,100 A | 8/1991 | Bar et al. | |
| 5,095,570 A | 3/1992 | Bar et al. | |
| 5,203,793 A | 4/1993 | Lyden | |
| 5,275,775 A | 1/1994 | Riecken | |
| 5,647,147 A | 7/1997 | Coomer | |
| 5,846,063 A | 12/1998 | Lakic | |
| 2004/0003514 A1 * | 1/2004 | Cole | A43B 7/142 36/43 |

* cited by examiner

PREFORM AND DEVICE FOR COOPERATION WITH A LOWER LIMB MEMBER, APPARATUS AND METHOD FOR MANUFACTURING THE DEVICE

FIELD OF THE INVENTION

The present invention relates to the field of support devices and orthotics. More particularly, it concerns an support device which can be manufactured during a single visit to an orthotist.

BACKGROUND OF THE INVENTION

Orthoses and support devices are technical aids destined to supplement or correct a deficiency or to compensate for a limitation, or even to increase the physiological performance of a member which has lost its function, has never fully developed, or is affected by a congenital anomaly.

Foot orthoses, for example, are generally used to correct different types of malfunctions, such as high arch or a flat foot. A patient requiring an orthosis typically needs to visit an orthotist at least twice in order to receive his or her orthosis. During the first visit, the orthotist will evaluate the patient and proceed with a print or impression of the foot of the patient. During the process of taking the imprint of the patient's foot, different types of forces need to be applied to the foot in order to understand the correction required, and these forces are very difficult to measure when not impossible. These forces often interfere with the apparatus used to take the prints or impressions of the foot. The corrections required for a numerical imprint are often based on a pre-established computer model which does not take into account the different characteristics of the patient's foot. In addition, modifications or adjustments to be made to the orthotics are usually made using percentages, which makes it difficult to perform the sometimes specific and particular corrections which are required but which are usually not compatible with the pre-established model.

Once a model of the orthosis is numerically obtained, the orthosis is usually manufactured externally in specialized laboratories, or the manufacturing can be done on the orthotist's premises using a specialized machine. Once the orthosis is made, the patient needs to return to the orthotist for at least one more visit so as to try on the orthosis and to determine whether the orthotist needs to further modify or adapt the orthosis to the patient's foot. This modification may be done by sanding or grinding the orthosis until the desired shape is obtained.

U.S. Pat. No. 4,470,782 to ZIMMERMANN describes an apparatus from producing custom orthoses which include a flat substrate pad and an elastic skin to form an expandable interior chamber. Drive pins are put in contact with the arch of a patient in order to maintain the foot in proper alignment for the injection of a moulding material.

The following US patents are also known to the Applicant: U.S. Pat. Nos. 5,275,775; 5,203,793; 5,095,570; 5,042,100; 4,962,762; 4,211,019; 4,128,951; 3,444,586 and 3,121,430.

In light of the preceding, there is a need for a preform which can be used in the making of an orthosis, and which can be manufactured during a single visit to the orthotist. There is also a need for an orthosis which can be easily adjusted and corrected so as to match the specific characteristics of each patient's foot. There is also a need for a process or method for manufacturing such an orthosis, and for an apparatus for manufacturing the orthosis. It would also be desirable if the orthosis could remain inexpensive and easy to manufacture.

SUMMARY OF THE INVENTION

It is an object of the present invention to provide an orthosis, a preform for an orthosis, an apparatus and a method of manufacturing that satisfies at least one of the above-mentioned needs.

In accordance with the present invention, the above-mentioned object is achieved with a preform for the manufacture of a device which cooperates with a lower limb member so as to provide a correction.

The preform comprises a base having a concave top face and a second face, the base being provided with at least one channel. The at least one channel has a first end opening on the top face, and a second end opening on the second face. The preform also has a surface linked to the top face of the base, for cooperation with the lower limb and at least one inflatable chamber formed by a flexible and liquid-impervious membrane sealed to the concave top face of the base.

The first end of the at least one channel is in fluid communication with the inflatable chamber, and the second end of the at least one channel is configured for connecting with an injection device, thereby allowing injection of a fluid composition of curable material while the lower limb member is in contact with the surface so as to inflate said at least one inflatable chamber until the correction is obtained, the composition being then cured in-situ into a cured material.

Preferably, the base is a sole and the lower limb member is a foot.

Preferably, the surface is part of the membrane.

Preferably, the at least one inflatable chamber is located over a predetermined portion of the top face of the base.

Preferably, the at least one inflatable chamber comprises a transitional chamber and at least one corrective chamber located within the transitional chamber. The at least one channel comprises one or several transitional chamber channels and one or several corrective channels. The transitional chamber is in fluid communication with one or several of said transitional chamber channels; and the corrective chamber or each of the corrective chambers is/are in fluid communication with one or several of said corrective channels.

Preferably, the top face of the sole comprises at least one of: a metatarsal zone, an internal arch zone, and an external arch zone, each zone being bordered by a corresponding perimeter, the membrane being sealed along said perimeter for forming the at least one corrective chamber.

Preferably, the preform comprises several corrective chambers, and the top face of the sole comprises several zones, each zone being associated with a corresponding one of the corrective chambers, each zone being bordered by a corresponding perimeter. The membrane is sealed along the perimeter of one of the zones for forming one of the corrective chambers. The preform includes additional membranes, each for forming a respective one of the remaining corrective chambers.

Preferably, the base comprises an extended zone encompassing said at least one of the metatarsal zone, the internal arch zone and the external arch zone. The preform comprises a second flexible and liquid-impervious membrane sealed along the perimeter of said extended zone for forming the transitional inflatable chamber.

Preferably, the membrane is one of laser-sealed, glue-sealed and heat-sealed to the base. Preferably, the membrane is gas-impervious. Still preferably, the membrane is gas-impervious and air-impervious.

Preferably, the at least one channel comprises at least one pair of first and second channels, the first channel being configured for injecting the fluid composition in the corresponding at least one inflatable chamber, and the second channel being configured for allowing any fluid composition in excess to exit the chamber.

According to another aspect of the invention, a device is provided. The device comprises a preform as defined above, wherein the at least one inflatable chamber is filled with the cured material.

Preferably, the curable material is cured at room temperature.

Preferably, the curable material is prepared extemporaneously by mixing two components in a fluidic state to obtain a resulting mixture that will remain in a fluidic state for a period varying from 3 to 20 minutes before curing into a cured material.

Preferably, the fluid composition is a polyurethane curable composition.

Preferably, the fluid composition is a two-component room temperature curing composition.

According to another aspect of the invention, there is provided an apparatus for manufacturing a device cooperating with a lower limb member for providing a correction. The apparatus comprises a receptacle for receiving a preform as defined above, as well as the lower limb member of a patient. The apparatus also comprises an injection system for injecting the fluid composition in order to inflate the at least one inflatable chamber until the correction is obtained, the composition being cured into the cured material while the lower limb member and the perform are still within the receptacle.

Preferably, the apparatus comprises a vacuum system for creating a vacuum in the at least one inflatable chamber of the preform prior to injecting the fluid composition.

Preferably, the apparatus comprises at least one cartridge for storing the fluid composition of curable material.

Preferably, the at least one cartridge includes two containers, each container containing a component of the fluid composition.

Preferably, the apparatus comprises pressure controlling means for controlling a pressure when injecting said fluid composition into the at least one inflatable chamber. Preferably, the receptacle comprises positioning means for positioning the lower limb member to a molding position.

Preferably, the injection system includes:
a push rod cooperating with a first end of the cartridge, for pushing the two components through the static mixer;
an injection tubing assembly having an injection inlet connected to an outlet of the static mixer, and one or several injection outlet(s), each connectable to a corresponding second channel of the preform; and
one or several valves, each associated with a corresponding injection outlet(s), for closing or opening said corresponding injection outlet(s).

Preferably, the vacuum system includes:
a vacuum device;
a vacuum tubing assembly, the vacuum tubing assembly having a vacuum inlet operatively connected to the vacuum device, and one or several vacuum outlet(s), each connectable to a corresponding first channel of the preform; and
one or several valves, each associated with a corresponding vacuum outlet(s), for closing or opening said corresponding vacuum outlet(s);

Preferably, the vacuum system comprises a compartment located between the vacuum inlet and the one or several vacuum outlet(s), for collecting the fluid composition in excess or pumped out by the vacuum device.

According to yet another embodiment of the invention, a method is provided. The method is for manufacturing a device for cooperating with a lower limb member for providing a correction. The method comprises the steps of:
a) positioning the lower limb member in a receptacle previously provided with a preform as defined above;
b) injecting the fluid composition in said at least one inflatable chamber until the correction is obtained; and
c) allowing said composition to cure in-situ so as to form the cured material.

Preferably, there is also provided a method for manufacturing an orthosis. The method includes the steps of:
a) positioning the foot in a receptacle previously provided with a preform as defined above, and for which the membrane is gas-impervious;
b) injecting the fluid composition in said at least one corrective chamber until the orthopaedic correction is obtained;
c) injecting the fluid composition in said transitional chamber in order to smooth out the surface in contact with the foot; and
d) allowing said composition to cure in-situ so as to form the cured material.

Preferably, the method comprises a step of vacuuming the at least one inflatable chamber of the preform prior performing step b).

By a "fluid" composition, it is meant that the composition is capable of flowing.

Advantageously, the preform, the device, the apparatus and the method of manufacture allow a patient to obtain a device for cooperation with a lower limb during a single visit to his or her orthotist. The device can be manufactured rapidly, easily and at low cost. The manufacturing of the device allows for a finer and more precise adjustment of the corrections to be made, and saves both the patient and the orthotist precious time. Another advantage of a device created from the preform is that it can provide a full contact of a portion of the lower limb member with the surface of the device. Yet another advantage is that is allows to distribute the load forces on said portion of the lower limb member.

BRIEF DESCRIPTION OF THE DRAWINGS

Other objects, advantages and features of the present invention will become more apparent upon reading the following non-restrictive description of preferred embodiments thereof, given for the purpose of exemplification only, with reference to the accompanying drawings in which.

DESCRIPTION OF PREFERRED EMBODIMENTS

Figure 1:
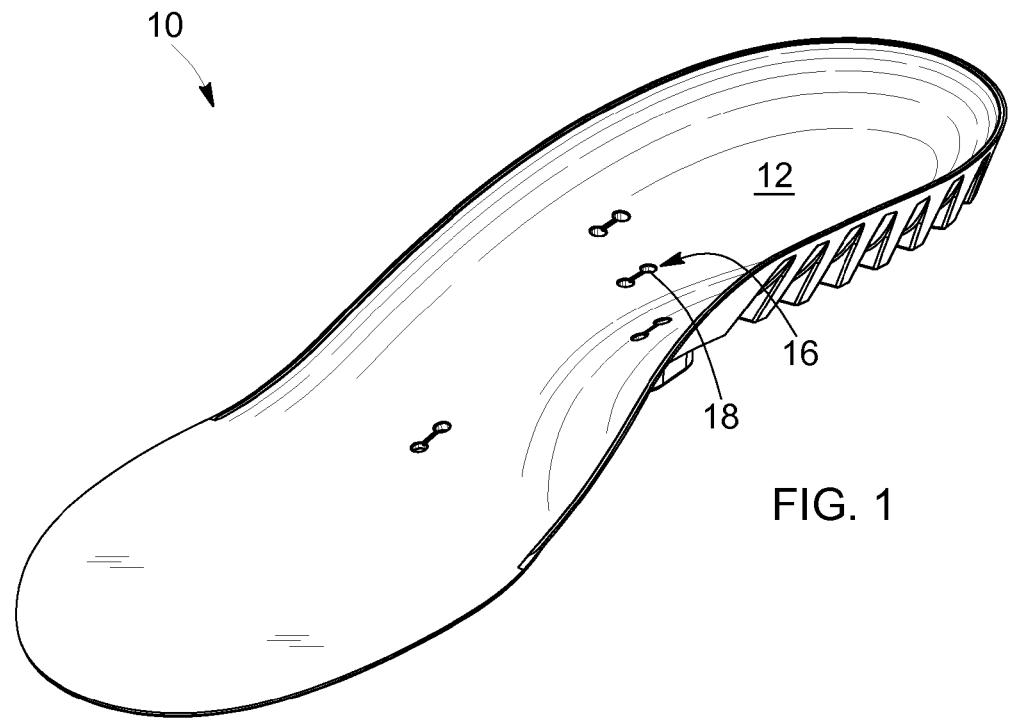
FIG. 1 is a top perspective view of a base for a preform, according to an embodiment of the invention.

In the following description, similar features in the drawings have been given similar reference numerals. For the sake of clarity, certain reference numerals have been omitted from the figures if they have already been identified in a preceding figure.

Preform and Device

Figure 2:
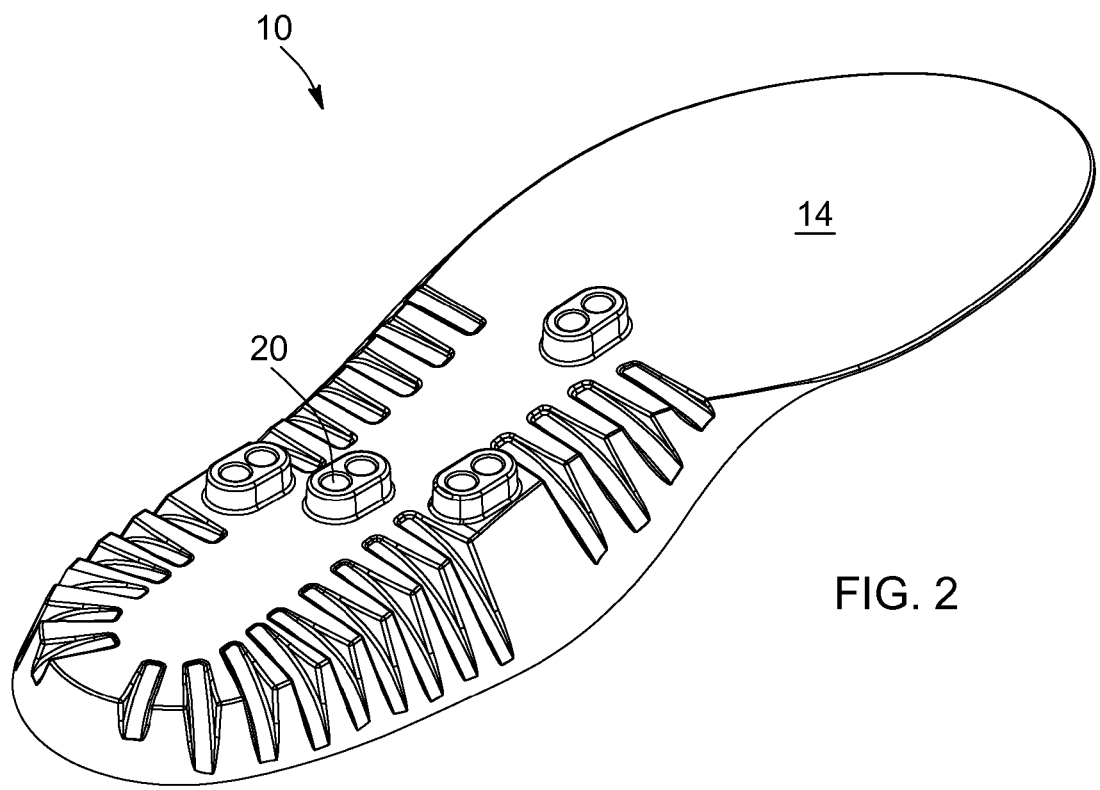
FIG. 2 is a bottom perspective view of the base of FIG. 1.

With reference to FIGS. 1 and 2, a base 10 is shown. The base 10 has a concave top face 12 and a second face 14, which is preferably a bottom face. The base 10 is provided with at least one channel 16, having a first end 18 opening on the top face 12, and a second end 20 opening on the second face 14. While in the case illustrated the second end 20 opens on the bottom face, it is understood to locate the second open end 20 on a side face of the base. While in the present case, the base is shaped as a sole, the base can take other shapes. The base can be shaped as a saucer, for example, when used as part of a socket for use in or with a prosthesis.

The base can be made of a variety of materials, such as either one of Ethylene-Vinyl-Acetate (EVA), Polyethylene, Polyuretane or a mix of these materials. The base can be manufactured from a foamed composition, for obtaining a lighter base, and is preferably made from injection molding. Preferably, the hardness of the base is between 30 and 80 on the Shore A scale. The base is flexible while providing adequate support, and it is light, preferably between 20 and 100 g. Preferably, the base is made of LARIPUR™ LPR 7560, which is a thermoplastic polyurethane (TPU) having a Shore A rating of 77.

Figure 3:
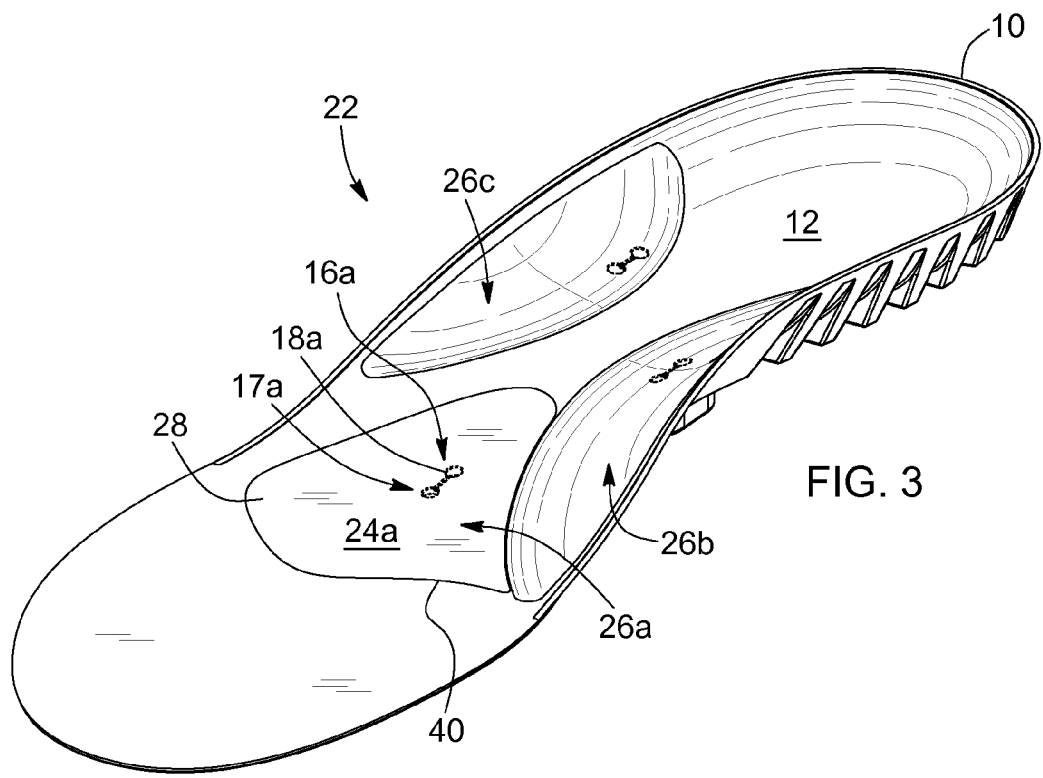
FIG. 3 is a top perspective view of a preform, according to an embodiment of the invention.

Referring to FIG. 3, a preform 22 is shown. The preform 22 can be used for the manufacture of a support device, which can be used in many different applications. In the present case, the preform is for the manufacture of an orthosis, also known as orthotic. By orthosis, it is meant a device, such as a brace or splint, for supporting, immobilizing, or treating muscles, joints, or skeletal parts which are weak, ineffective, deformed, or injured.

Alternatively, the preform of the invention can also be used for the manufacture of a socket, as part of a prosthesis. A prosthesis socket is used for connecting a residual limb, or stump, to a prosthesis, for ensuring adequate support and a good fit for the prosthesis.

The device thus cooperates with a lower limb member, and is intended to provide a correction. The correction can be an orthopaedic correction, or it can simply be an adjustment made for improving the comfort of the lower limb member. A lower limb member can be for example a knee, a foot, a leg, a stump or any member which supports weight.

Still referring to FIG. 3, the preform 22 includes a base 10 and a surface 24 linked to the top face 12 of the base 10. The surface 24 cooperates with a lower limb, which is in this case would be a foot. The preform 22 includes at least one inflatable chamber 26a, formed by a flexible and liquid-impervious membrane 28. The membrane 28 is sealed to the concave top face 12 of the base 10. The first end 18a of the channel 16a is in fluid communication with the inflatable chamber 26a, and the second end of the channel 16a, located on the bottom face of the base 10, is for connection with an injection device, for allowing injection of a fluid composition of curable material within the chamber 26a. The injection is to be made while the lower limb member is in contact with the surface 24a, for inflating the chamber 26a until the correction is obtained, the composition being then cured in-situ into a cured material. While it can be considered to have only one channel per chamber, it is preferable to have at least one pair of first and second channels 16a, 17a in fluid communication with a chamber. In chamber 26a, the first channel 16a is for injecting the fluid composition in the inflatable chamber 26a, and the second channel 17a is for allowing any fluid composition in excess to exit the chamber 26a.

In the present case, the surface 24a is part of the membrane 28. The membrane 28 is sealed on the base 10 along a perimeter 40, delimiting a zone, for forming the chamber 26a. It can be laser-sealed, glue-sealed or heat-sealed to the top face 12. A seal made by laser is preferred, because it provides a finer and more precise seal joint. In this embodiment, the preform 22 includes three inflatable chambers 26a, 26b and 26c. The same membrane 28 can be used for forming the three chambers 26a, 26b and 26c. In this case the membrane is sealed along the three distinct perimeters delineating the chambers, the membrane then being cut on the outer side of the joint. Alternatively, each chamber 26a, 26b and 26c can be made using a different membrane.

FIG. 3 shows the membrane 28 made of a transparent material so as to visualise the first end 18a of the channel 16a underneath the membrane 28. However, the membrane 28 can be considered to be made of an opaque material instead. The chamber 26a does not extend over the entire top face 12. It is located over a predetermined portion of the top face 12 of the base 10.

The membrane 24 is preferably extendible in multiple directions. It is resistant to tearing, and is relatively thin. It is also resilient, and is made of a material which can be sealed or glued with the base 10. The hardness of the membrane is between about 30 and 70 on the A Shore scale, and most preferably between about 40 and 50. If the membrane is to be glued to the base, materials such as silicone, rubber and polyurethane can be used for the membrane. If the membrane is to be laser-sealed on the base, than thermoplastic polyurethane (TPU) is preferred. Preferably, the membrane is DT-7101™ manufactured by Polyfilm Inc. This membrane as a hardness between about 60 and 70 A Shore, an ultimate elongation of 730%, and can be laser-sealed to a base made of LARIPUR™ LPR 7560. Its preferred thickness is about 4 to 6 thousandths of an inch. In the case where the membrane is laser-sealed, then the membrane should be laser-transparent, without any carbon black.

Figure 4:
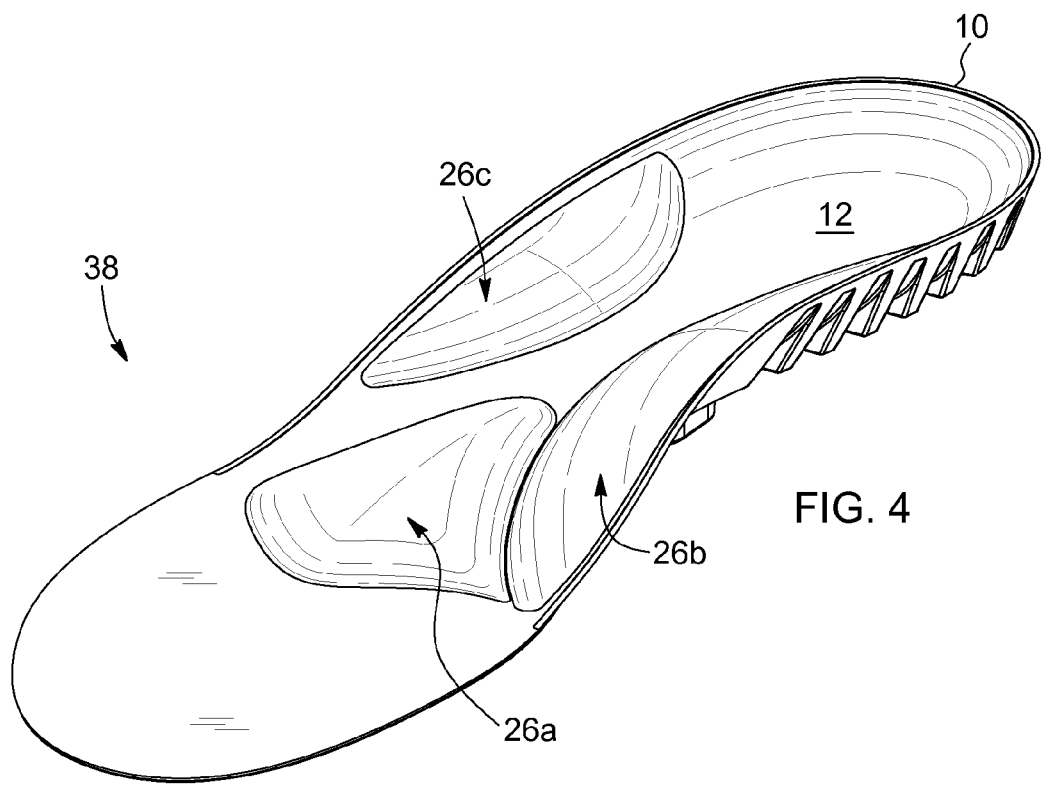
FIG. 4 is a top perspective view of a device made from the preform of FIG. 3, according to an embodiment of the invention.

Referring to FIG. 4, a support device 38 including the preform 22 of FIG. 3 is shown, with at least one inflatable chamber 26a filled with the cured material. In the present case, the support device 38 is a foot orthosis, and all three inflatable chambers 26a, 26b and 26c are filled with cured material. As explained earlier, the device 38 is for cooperating with a lower limb member for providing a correction, or an adjustment. The correction can consist for example of a realignment of the lower limb member or an elevation of portions of the member.

Figure 5:
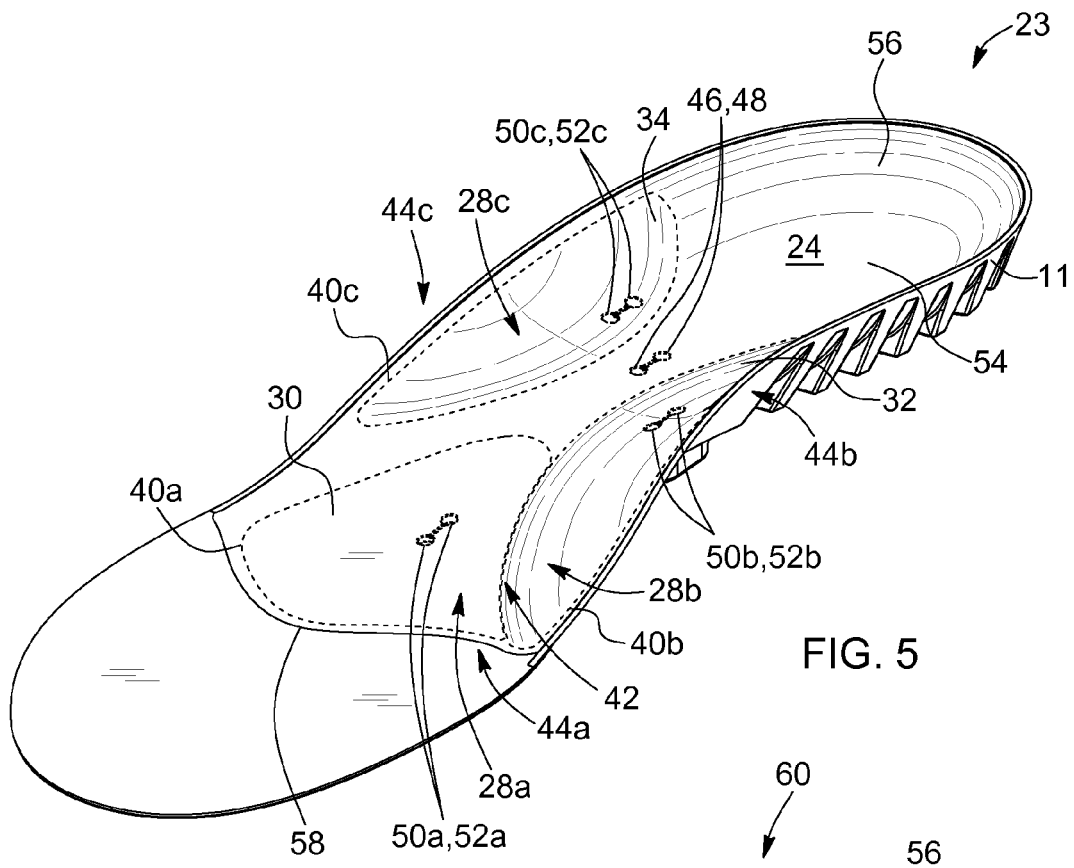
FIG. 5 is a top perspective view of a preform, according to another embodiment of the invention.

Referring now to FIG. 5, another embodiment of a preform is shown. The preform 23 includes a transitional chamber 42 and at least one corrective chamber 44a located within the transitional chamber 42. In the present case, the preform 23 includes three corrective chambers 44a, 44b and 44c. The base or sole 11 is provided with at least one transitional chamber channel 46 and one or several corrective chamber channels 48a, 48b and 48c. In the present case, each chamber 42, 44a, 44b, 44c is provided with a pair of channels. There is a pair of first and second transitional chamber channels 46, 48, and three pairs of first and second corrective chamber channels 50, 52. The transitional chamber 42 is in fluid communication with the transitional chamber channels 46, 48 and each of the corrective chambers 44a, 44b, 44c is in fluid communication with one of the corrective chamber channels 50, 52.

The top face of the base 10 includes at least one of a metatarsal zone 30, an internal arch zone 32, and an external arch zone 34, each zone being bordered by a corresponding perimeter 40a, 40b or 40c. A membrane 28a, 28b, 28c is sealed along the corresponding perimeters 40a, 40b and 40c for forming the least one corrective chamber 44a, and in this embodiment, the three corrective chambers 44a, 44b and 44c. The same membrane 28 can be used for forming all three corrective chambers 44a, 44b and 44c, or each corrective chamber 44a, 44b or 44c can be formed with distinct or additional membranes.

Still referring to FIG. 5, the base or sole 11 includes an extended zone 54 encompassing at least one of the metatarsal zone 30, the internal arch zone 32 and the external arch zone 34. The preform 23 is also provided with a second flexible and liquid-impervious membrane 56 sealed to the sole 11 along the perimeter 58 of the extended zone 54 for forming the transitional inflatable chamber 42. In the illustrated embodiment, the surface 24 is part of this second membrane 56. The second membrane 56 extends over a large—or extended—zone 54 covering sole 11 almost entirely, except for its distal or front end. This extended zone 54 is delimited by the outer perimeter of the sole 11 on the sides and back end of the sole 11, and by the metatarsal zone 30 at the front end of the sole. The membranes 28 and 56 are preferably gas-impervious. Preferably, they are also liquid-impervious. In order to adequately respond to each patient's needs, the preform comes in various sizes, each size preferably covering two shoe sizes.

In the case where the preform is used as a socket for prosthesis, the base can also be provided with one or several zones provided with corresponding corrective chambers. The specific zones can correspond to different portions of a stump, and the preform can be provided with a transitional chamber including the corrective chamber(s).

Figure 6:
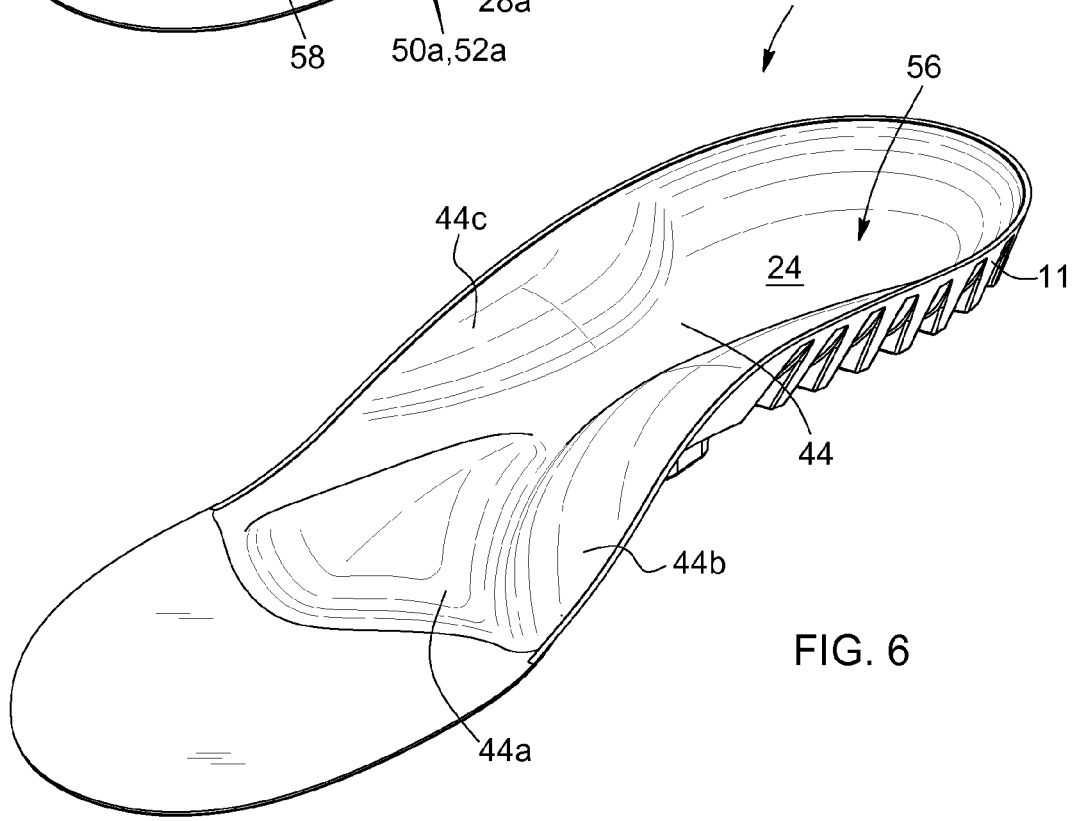
FIG. 6 is a top perspective view of a device made from the preform of FIG. 5, according to another embodiment of the invention.
Figure 7:
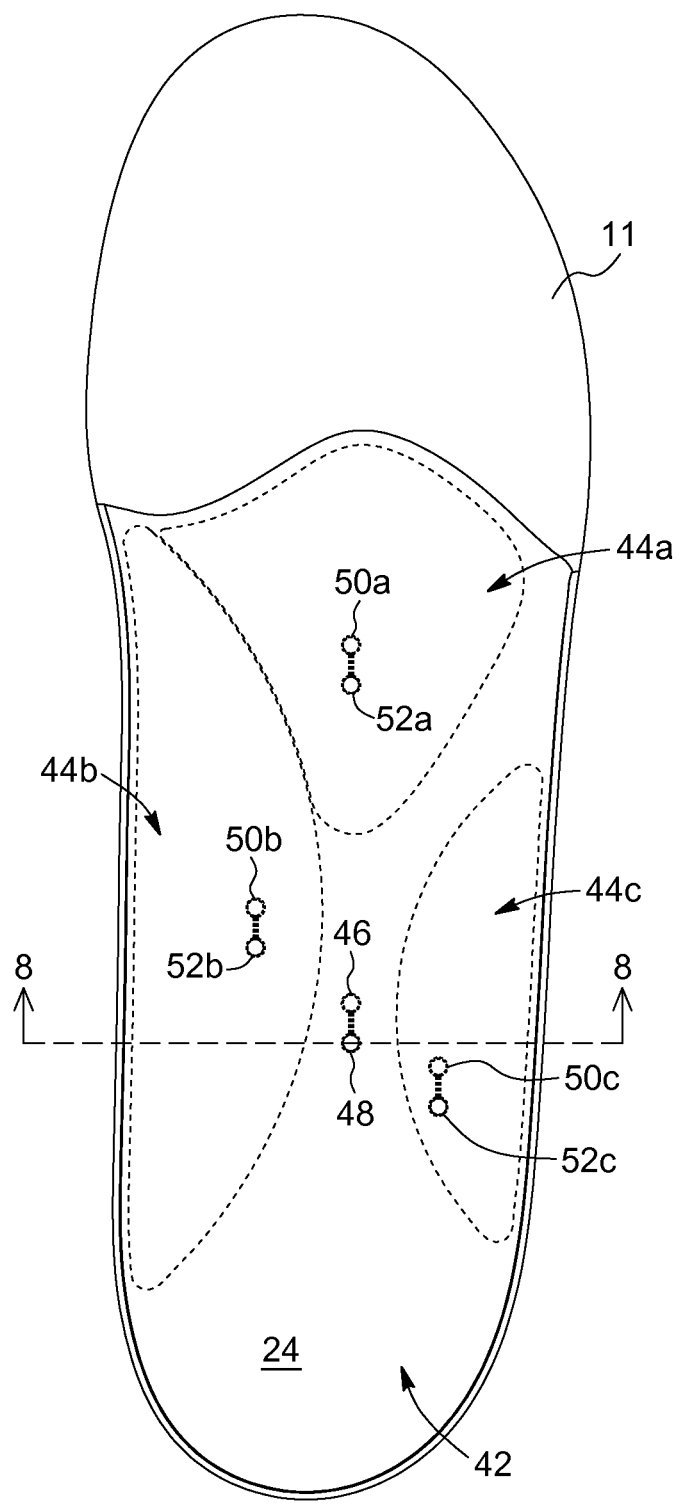
FIG. 7 is a top view of a preform, according to an embodiment of the invention.
Figure 8A:
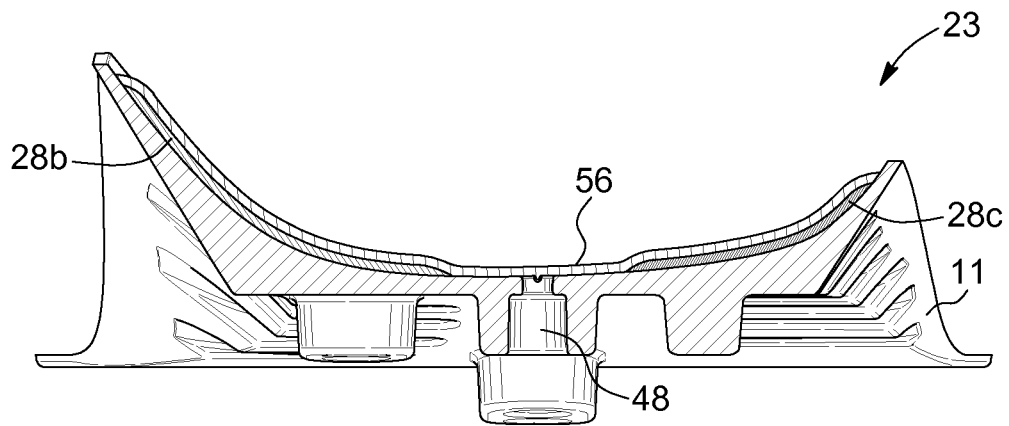
FIG. 8A is a cross-sectional view of FIG. 7 taken along line 8-8, with the chambers deflated, according to an embodiment of the invention.
Figure 8B:
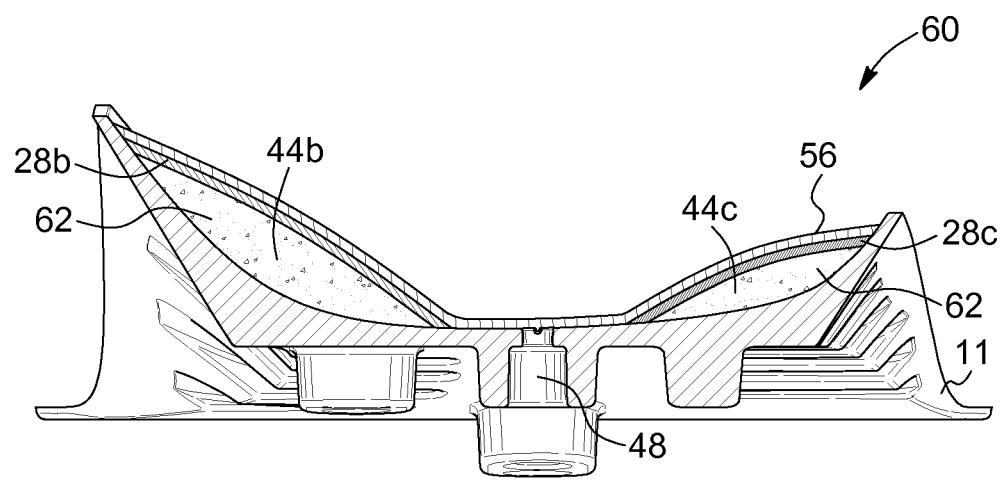
FIG. 8B is a cross-sectional view of FIG. 7 taken along line 8-8, with some of the chambers inflated, according to an embodiment of the invention.
Figure 8C:
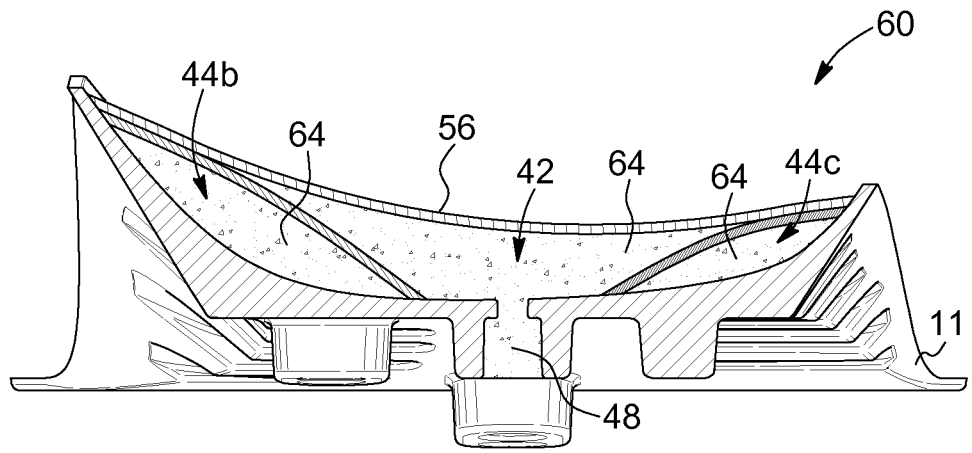
FIG. 8C is a cross-sectional view of FIG. 7 taken along line 8-8, with the chambers filed, according to an embodiment of the invention.

With reference to FIG. 6, an orthosis 60 made from the preform 23 is shown, with at least one inflatable chamber filled with the cured material. In the present case, all three corrective chambers 44a, 44b, 44c are filled with cured material, as well as the transitional chamber 42. The curable material preferably cures at room temperature. The curable material is also preferably prepared extemporaneously by mixing two components in a fluidic state, to obtain a resulting mixture that will remain in a fluidic state for a period varying from 5 to 20 minutes before curing into a cured material. A polyurethane curable composition can be used. The fluid composition is also preferably a two-component room temperature curing composition.

More specifically, it is preferable to use a thermosetting composition made of components A and B, which is as fluid as possible and which cures rapidly. A fluid composition including polyurtherane or silicone can be considered. Optionally, one of the components can further comprise a catalyst to induce or accelerate the curing process. Using a retardant can also be considered. When mixed, the viscosity of the resulting fluid composition should stay relatively low and stable for 3 to 20 minutes, and preferably between 4 and 5 minutes, and must set or cure rapidly, between 8 to 25 minutes, and preferably between 8 to 12 minutes, after mixing the components. Preferably the fluid composition viscosity is from 1 to 20,000 mPas. The setting temperature should be between 20 and 35° C., and is preferably between 27° C. to 30° C. Since the injection is preferably done under vacuum, as will be explained in more detail later on in the description, no gas should emanate from the mixed composition. The fluid composition and the resulting cured material preferably adhere strongly to the inner face of the membrane 28 and/or 56 forming the chambers, the membrane being preferably made of thermoplastic polyurethane (TPU). The hardness of the cured material is preferably between 0 and 50 on the Shore A scale, with a density of about 1 g/cm$^3$. Of course, it may be possible to lower said density by using other types of material by the using lighter filler material within the fluid. Gyftane™ P20100sp can be used as the fluid composition. It has a Shore A rating varying between 0 to 95, an elongation percentage of 1150% at 170 psi, and has a set time varying between 2 to 10 minutes.

Still referring to FIG. 6, the surface 24 devised to contact the foot of the patient corresponds to the top face of the second membrane 56. The transitional chamber 42 advantageously provides a smooth transition between the different corrective chambers 44a, 44b and 44c, increasing the comfort of the patient when using the orthosis 60.

The method and the apparatus 70 used for manufacturing the device will now be described with reference to FIGS. 7, 8A to 8C, 9 and 10. It should be noted that the cover plate of the apparatus 70 in FIG. 9 has been removed in order to better visualize internal components therein.

During a first step, the lower limb is positioned in a receptacle 72 previously provided with a preform 23. The lower limb is put in contact with the surface 24 of the preform 23. Preferably, the lower limb member is maintained in a neutral position. The neutral position can be the position in which the member is aligned or raised correctly. If the neutral position cannot be reached, the member is placed in a desired position which is as close as possible to the neutral position. The patient is preferably standing when positioning the lower limb member over the preform. It allows better understanding and appreciating how the preform, which will eventually form the device, reacts when submitted to the load of the patient. It also allows maintaining the foot in either one of a neutral position, semi-loaded position or full-loaded position. The orthotist or podiatrist ensures, using positioning means or a positioning system, that the foot of the patient adequately contacts the preform 23, especially the sides of the preform 23. Guides can be provided with a mold for adequately positioning the foot within the receptacle 72.

During this first step, the corrective and transitional chambers 44, 42 are deflated, the membrane 28 of the corrective chamber being in contact with the membrane 56 of the transitional chamber. Preferably, the chambers 44, 42 are vacuumed prior to the injection of the fluid composition 62 in the chambers. The vacuuming of the chambers 44, 42 ensures that no air is left in the chambers once the support device is formed, which would otherwise leave gas bubble in the chambers. Of course, while the preform 23 is provided with a transitional chamber 42, it can also be considered to use a preform without a transitional chamber. Generally stated, the second step of the method consists of injecting the fluid composition 62 in at least one inflatable chamber until the correction is obtained. In a third step, the composition is allowed to cure "in-situ" into the cured material. The method and apparatus will be explained in more detail below.

The apparatus 70 includes at least one cartridge 88 for storing the fluid composition of curable material. In the case where thermosetting components A and B are used, the cartridge 88 includes two containers 90, each containing one of the two components of the fluid composition. The cartridge 88 has first and second ends, the cartridge 88 including a static mixer 92 provided with an outlet at the second end of the cartridge. The injection system 76 includes a push rod 94, an injection tubing assembly 96, and one or several injection valves 100. The push rod 94 cooperates with the first end of the cartridge 88, for pushing the two components through the static mixer 92. The injection tubing assembly 96 has an injection inlet connected to the outlet of the static mixer 94, and one or several injection outlets 98, each connectable to a corresponding second channel 52a, 52b, 52c of the preform. Each valve 100 is associated with a corresponding injection outlet 98 for closing or opening the injection outlet 98 in question. The injection of the fluid composition 62 can thus be controlled with the valves 100. Preferably, the apparatus includes controlling means 102 for controlling a pressure while injecting the fluid composition in the inflatable chambers.

In the present case, when the preform 23 is provided with both corrective and transitional chambers 44, 42, the fluid composition is first injected in at least one of the corrective chambers 44a, 44b and/or 44c, using an injecting system 74.

Figure 9:
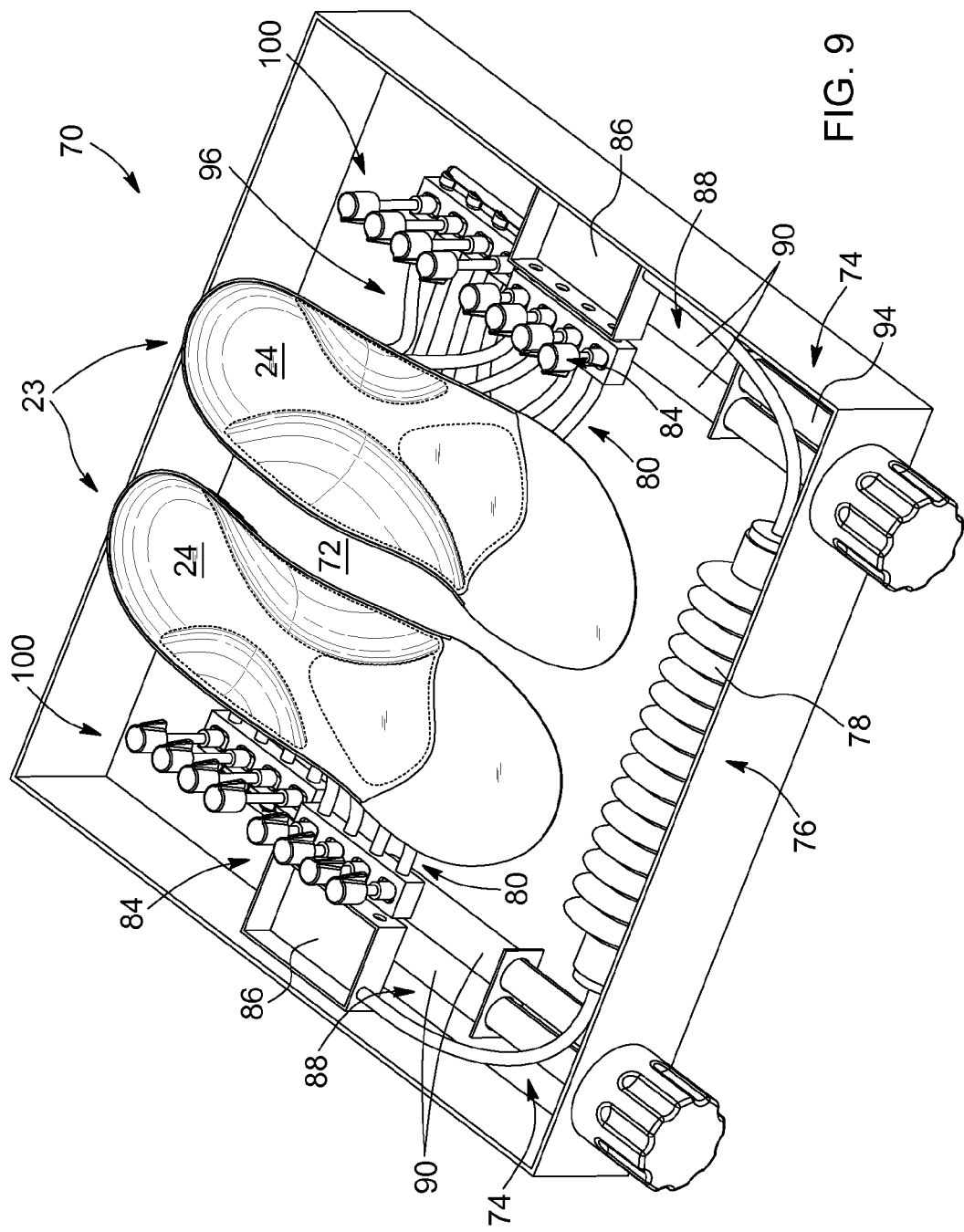
FIG. 9 is a top perspective view of an apparatus, according to an embodiment of the invention.
Figure 10:
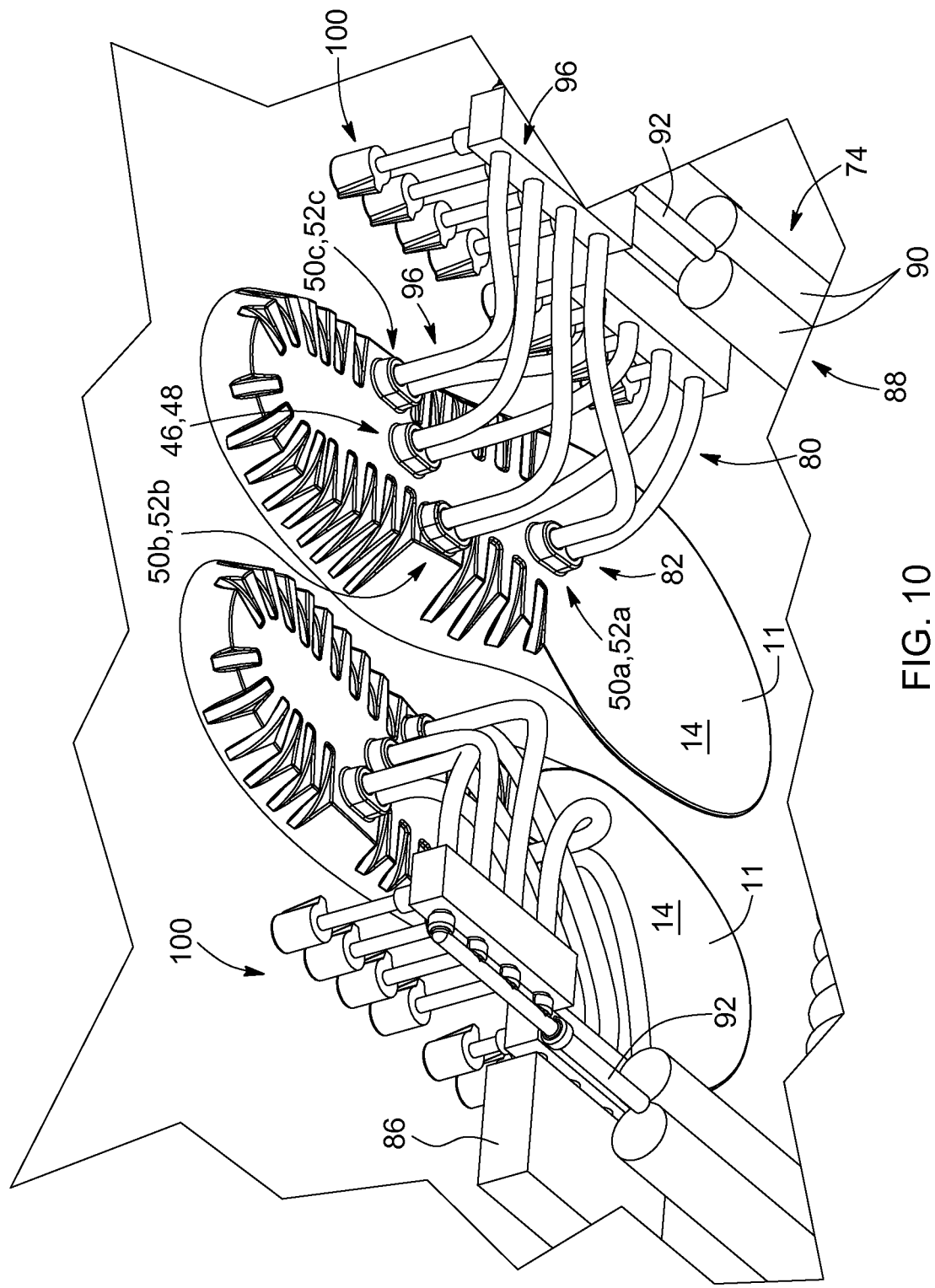
FIG. 10 is a bottom view of some components of the apparatus of FIG. 9, according to an embodiment of the invention.

With reference to FIGS. 9 and 10, the chambers 44a, 44b and/or 44c are first vacuumed by connecting a vacuum system 76 to each of the second end of the first corrective chamber channels 50a, 50b, 50c, these second ends being located underneath the base 11. The vacuum system 76, which is preferably part of the apparatus 70, includes a vacuum device 78, a vacuum tubing assembly 80, one or several vacuum outlet(s) 82, and one or several valves 84. The vacuum device 78 can be for example a pump. The vacuum tubing assembly 80 has a vacuum inlet operatively connected to the vacuum device 78, and one or several vacuum outlets, each connectable to a corresponding first channel 50a, 50b, 50c of the preform. Each valve 84 is associated with a corresponding vacuum outlet 82 for closing or opening the corresponding vacuum outlet 82. The valves 84 allow controlling vacuuming of the chambers 44, 42 individually. Preferably, the vacuum system 76 also includes a collecting compartment 86, located between the vacuum inlet and the vacuum outlets 82, for collecting fluid composition in excess, or pumped out by the vacuum device 78, as will be explained below. The collecting compartment 86 is shown in FIG. 9 without a cover, in order to better illustrate how it connects the valves 84. Of course, during use, the collecting compartment is closed and air tight for vacuuming the chambers. The cover is preferably made of transparent material, in order to see if fluid is present in the collecting compartment or not. Of course, it can also be considered to provide the collecting compartment with a sensor or another detection device so as to detect the presence of fluid, instead of the transparent cover.

While maintaining the chambers 44a, 44b, 44c under vacuum, the fluid composition is injected in the corrective chambers through the second corrective chamber channels 52a, 52b and 52c by using the injection system 74, in order to inflate the chambers until the desired correction is obtained. This step is done while maintaining the lower limb member of the patient, which would be in this case a foot, in contact with the surface 24 of the preform 23.

The fluid 62 is injected by pushing the push rod 94, with the use of a turning knob or of any other convenient mechanism. Thermosetting components A and B are stored in separate containers 90a, 90b of the cartridge 88, and are pushed in the static mixer 92 to be mixed for forming the fluid composition. Each valve 84 associated with a corresponding corrective chamber 44 and placed in the open position, while maintaining the valve associated with the transitional chamber 42 closed. The fluid composition first fills the second channels 52a, 52b, 52c, then fills the chambers 44a, 44b, 44c and eventually fills the first channels 50a, 50b and 50c. Fluid exiting the first channels 50a, 50b and 50c is collected in the collecting compartment 78, which is connected to the vacuum system 76. This operation ensures that there is no residual air in the corrective chambers, and that they are completely filled with the fluid composition 62. When fluid is detected in the collecting compartment, the vacuum device 78 can be stopped, and the vacuum valves closed. The injection of fluid will continue until the desired correction or adjustment is obtained. If too much fluid has filled a given corrective chamber, the fluid in excess can be squeezed out manually, ensuring that the vacuum valve corresponding to this given chamber is opened while the valves are closed, or alternatively the vacuum device can be restarted. The fluid in excess is collected in the collecting compartment 78. The volume of fluid within each chamber can thus be adjusted until the correction is obtained. This adjustment process is preferably conducted while the fluid composition still has a high viscosity, and while the curing process is not too advanced. Once the corrective chambers have a volume providing the correction, the injection valves 100 associated with the corrective chambers are closed, as well as the vacuum valves 84. Since the chambers 44 are independent from one another, they can each be filled and inflated independently with the fluid composition 62 comprising the curable components, until the desired volume is reached.

Once the corrective chambers are filled, injection of the fluid composition in the transitional chamber is performed, in order to smooth out the surface in contact with the foot. More specifically, the vacuum device 78 is started and the valve corresponding to the transitional chamber 42 is opened. The transitional chamber is vacuumed. The injection valve corresponding to the transitional chamber 42 is opened, and the push rod 94 is further pushed to inject the fluid composition in the transitional chamber 42. The fluid first fills the second transitional chamber channel 48, then fills the chamber 42, and then fills the first transitional chamber channel 46 until fluid exits the preform in the collecting compartment 86. The vacuum device 78 can be stopped at that point, and the vacuum valve closed. The injection of fluid is continued until the transitional chamber 42 smoothes out the relief of the top face of the orthosis. Adjustment to the volume of fluid present in the chamber 42 can be made, using the same steps as described above for the corrective chambers. Both the vacuum and the injection valves corresponding to the transitional chamber are then closed, and the fluid composition is allowed to cure "in-situ" into the cured material. The transitional chamber advantageously links the corrective chambers, and provides a more uniform and even contact surface with the lower limb member of the patient, increasing comfort of the patient when wearing or using the device. Inflating the transitional chamber 42 allows a larger surface of the foot to be in contact with the orthosis 38—and ideally a complete and total contact of the foot with the orthosis 38. As mentioned earlier, the use and filling of a transitional chamber is optional.

Figure 11:
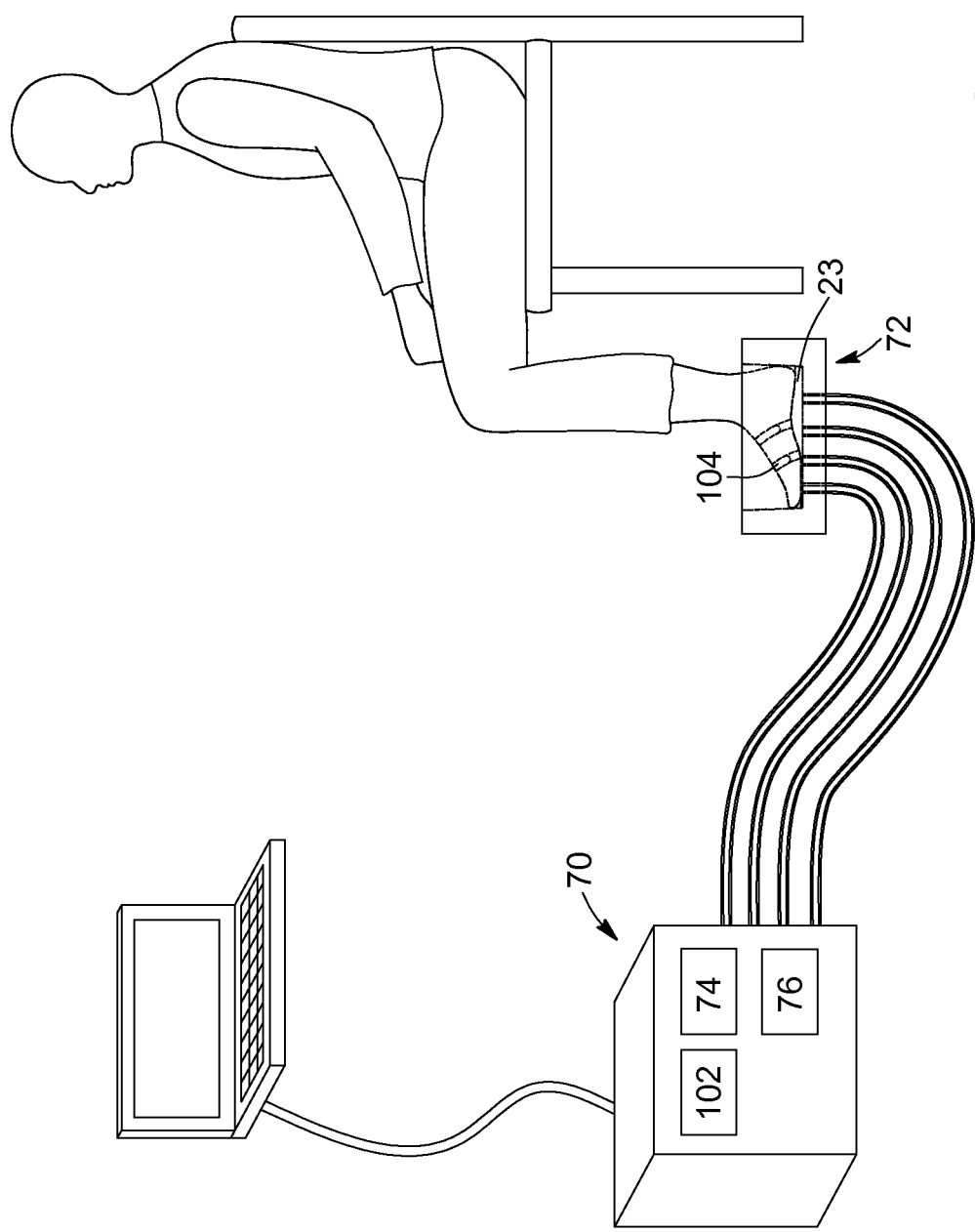
FIG. 11 is a schematic representation of an apparatus for manufacturing the device, according to an embodiment of the invention.

Now referring to FIG. 11, another embodiment of an apparatus 70 is shown. The apparatus includes an injection system 74 and a vacuum system 76 similar to the one described above. The apparatus 70 further comprises a pressure control system 102, including pressure sensor(s) and a pressure controller for monitoring and controlling the pressure of the fluid within each inflatable chamber. The pressure sensor(s) can be placed within the chambers, or alternatively in cooperation with the injection tubing assembly, or the injection valves. Information from the pressure sensors can be relayed to the pressure controller, which can be for example linked to part of a computer station.

It is also preferable to provide the receptacle with positioning means for positioning the lower limb member in the moulding position, so as to achieve the desired correction with more ease. The positioning means also maintain the preform in contact with the lower limb member, especially on the periphery of the preform. In the case of a preform for forming a foot orthosis, it is sometimes necessary to have the internal arch zone adhere to the foot of the patient during the adjustment and curing steps of the manufacturing process. The position means can be for example straps, such as shown in FIG. 11, or plates or any other tool which can help maintain the preform in contact with the lower limb member of the patient.

Once the fluid 62 is cured, the patient can remove his foot from the receptacle 72 and the device 38 is ready to be used and worn, without the patient to make a return visit to the orthotist. The device 38 also has the advantage of not having to be corrected, reworked or adjusted once formed.

Of course, numerous modifications could be made to the embodiments above without departing from the scope of the present invention.

The invention claimed is:

1. A device for cooperating with a lower limb member comprising:
   a base having a concave top face and a second face, the base being provided with at least one channel, said at least one channel having a first end opening on the top face, and a second end opening on the second face;
   a surface linked to the top face of the base, for cooperation with the limb member; and
   at least one inflatable chamber formed by a flexible and liquid-impervious membrane sealed to the concave top face of the base,
the first end of said at least one channel being in fluid communication with said inflatable chamber, and the second end of said at least one channel being configured for connecting with an injection device, thereby allowing injection of a fluid composition of curable material while the lower limb member is in contact with the surface so as to inflate said at least one inflatable chamber, said composition being then cured in-situ into a cured material, wherein said at least one inflatable chamber comprises:
   a transitional chamber; and
   at least one corrective chamber located within the transitional chamber;
wherein said at least one channel comprises one or several transitional chamber channels and one or several corrective channels, wherein said transitional chamber is in fluid communication with one or several of said transitional chamber channels; and wherein the corrective chamber or each of said corrective chambers is/are in fluid communication with one or several of said corrective chamber channels.

2. The device according to claim 1, wherein the base is a sole, said lower limb member being a foot.

3. The device according to claim 1, wherein said surface is part of said membrane.

4. The device according to claim 1, wherein said at least one inflatable chamber is located over a predetermined portion of the top face of the base.

5. The device according to claim 4, wherein the top face of the base comprises at least one of: a metatarsal zone, an internal arch zone, and an external arch zone, each zone being bordered by a corresponding perimeter, said membrane being sealed along said perimeter for forming said at least one corrective chamber.

6. The device according to claim 1, comprising several corrective chambers, and wherein the top face of the base comprises several zones, each zone being associated with a corresponding one of the corrective chambers, each zone being bordered by a corresponding perimeter, said membrane being sealed along the perimeter of one of the zones for forming one of the corrective chambers, the device including additional membranes, each for forming a respective one of the remaining corrective chambers.

7. The device according to claim 5, wherein the base comprises an extended zone encompassing said at least one of the metatarsal zone, the internal arch zone and the external arch zone, the device comprising a second flexible and liquid-impervious membrane sealed along the perimeter of said extended zone for forming the transitional inflatable chamber.

8. The device according to claim 1, wherein said membrane is one of laser-sealed, glue-sealed and heat-sealed.

9. The device according to claim 1, wherein said membrane is gas-impervious.

10. The device according to claim 1, wherein said at least one channel comprises at least one pair of first and second channels, said first channel being for injecting said fluid composition in said corresponding at least one inflatable chamber, and said second channel being for allowing any fluid composition in excess to exit the chamber.

11. A device according to claim 1, wherein said at least one inflatable chamber is filled with the curable material.

12. The device according to claim 11, wherein the curable material is cured at room temperature.

13. The device according to claim 12, wherein the curable material is prepared extemporaneously by mixing two components in a fluidic state, to obtain a resulting mixture that will remain in a fluidic state for a period varying from 3 to 20 minutes before curing into a cured material.

14. The device according to claim 13, wherein the fluid composition is a polyurethane curable composition.

15. The device according to claim 12, wherein the fluid composition is a two-component room-temperature-curing composition.

16. An apparatus for manufacturing a device for cooperating with a lower limb member so as to provide a correction, said apparatus comprising:
   a receptacle for receiving a device as defined in claim 10 and the lower limb member; and
   an injection system for injecting the fluid composition in order to inflate said at least one inflatable chamber until the correction is obtained, the composition being cured into the cured material while the lower limb member and the perform are still within the receptacle.

17. The apparatus according to claim 16, further comprising a vacuum system for creating a vacuum in said at least one inflatable chamber of the device, prior to the injection of the fluid composition.

18. The apparatus according to claim 16, comprising at least one cartridge for storing the fluid composition of curable material.

19. The apparatus according to claim 18, wherein said at least one cartridge includes two containers for respectively containing two components of the fluid composition.

20. The apparatus according to claim 16, further comprising pressure controlling means for controlling a pressure when injecting said fluid composition in said at least one inflatable chamber.

21. The apparatus according to claim 16, wherein the receptacle comprises positioning means for positioning the lower limb member in a molding position.

22. The apparatus according to claim 20, wherein:
said at least one cartridge has first and second ends, said cartridge including a static mixer provided with an outlet at said second end;
said injection system includes:
a push rod cooperating with said first end of the cartridge, for pushing the two components through the static mixer;
an injection tubing assembly having an injection inlet connected to an outlet of the static mixer, and one or several injection outlet(s), each connectable to a corresponding second channel of the preform; and
one or several valves, each associated with a corresponding injection outlet(s), for closing or opening said corresponding injection outlet(s);
wherein said vacuum system includes:
a vacuum device;
a vacuum tubing assembly, said vacuum tubing assembly having an vacuum inlet operatively connected to the vacuum device, and one or several vacuum outlet(s), each connectable to a corresponding first channel of the preform; and
one or several valves, each associated with a corresponding vacuum outlet(s), for closing or opening said corresponding vacuum outlet(s).

23. The apparatus according to claim 22, wherein said vacuum system comprises a compartment located between said vacuum inlet and said one or several vacuum outlet(s), for collecting the fluid composition in excess or pumped out by the vacuum device.

24. A method for manufacturing a device for cooperating with a lower limb member so as to provide a correction, said method comprising the steps of:
a) positioning the lower limb member in a receptacle previously provided with a device as defined in claim 1;
b) injecting the fluid composition in said at least one inflatable chamber until the correction is obtained; and
c) allowing said composition to cure in-situ into the cured material.

25. A method for manufacturing an orthosis for cooperating with a foot for providing an orthopaedic correction, said method comprising the steps of:
a) positioning the foot in a receptacle previously provided with a device as defined in claim 9;
b) injecting the fluid composition in said at least one corrective chamber until the correction is obtained;
c) injecting the fluid composition in said transitional chamber in order to smooth out the surface in contact with the foot; and
d) allowing said composition to cure in-situ into the cured material.

26. The method according to claim 25, further comprising a step of vacuuming the at least one inflatable chamber of the device prior to performing step b).

27. The method according to claim 26, wherein step b) comprises a sub-step of monitoring and controlling the pressure of the fluid injected in said at least one chamber.

28. The method according to claim 27, comprising a step of mixing two polymeric components for obtaining the fluid composition of curable material, performed prior step b).

\* \* \* \* \*